(12) United States Patent
Pao et al.

(10) Patent No.: US 8,470,365 B2
(45) Date of Patent: Jun. 25, 2013

(54) PROCESS FOR PREPARATION OF ANTI-TUBERCULAR COMBINATION AND PHARMACEUTICAL COMPOSITION PREPARED THEREFROM

(75) Inventors: Li-Heng Pao, Taipei (TW); Nion-Heng Shiao, Taoyuan (TW); Kuo-Hua Yang, Taoyuan (TW); Jui-Ming Chou, Taipei (TW)

(73) Assignee: Taiwan Biotech Co., Ltd., Taipei (TW)

( * ) Notice: Subject to any disclaimer, the term of this patent is extended or adjusted under 35 U.S.C. 154(b) by 91 days.

(21) Appl. No.: 12/846,476

(22) Filed: Jul. 29, 2010

(65) Prior Publication Data

US 2012/0027853 A1 Feb. 2, 2012

(51) Int. Cl.
*A61K 9/20* (2006.01)

(52) U.S. Cl.
USPC ...... 424/464; 424/465; 514/254.11; 427/2.14

(58) Field of Classification Search
None
See application file for complete search history.

(56) References Cited

U.S. PATENT DOCUMENTS

| 7,195,769 | B2 | 3/2007 | Singh et al. | |
|---|---|---|---|---|
| 2003/0068366 | A1* | 4/2003 | Chungi et al. | 424/452 |
| 2005/0084455 | A1 | 4/2005 | Sen et al. | |
| 2005/0249804 | A1 | 11/2005 | Sapte | |

FOREIGN PATENT DOCUMENTS

| CN | 1390546 A | * | 1/2003 |
|---|---|---|---|
| CN | 1408354 | | 4/2003 |
| CN | 1437946 | | 8/2003 |
| CN | 1437946 A | * | 8/2003 |
| CN | 1201739 C | * | 5/2005 |
| WO | 02/087547 | | 11/2001 |

OTHER PUBLICATIONS

Bhise et al., "Design development and evaluation of Rifampicin delayed release tablets by using Sodium Lauryl Sulphate", Journal of Pharmacy Research, vol. 2, Issue 1, Jan. 2009, pp. 127-131.*

* cited by examiner

*Primary Examiner* — James H Alstrum Acevedo
*Assistant Examiner* — Daniel L Branson
(74) *Attorney, Agent, or Firm* — McDonnell Boehnen Hulbert & Berghoff LLP

(57) ABSTRACT

This invention relates to a process for preparing a pharmaceutical composition comprising four antitubercular drugs: rifampin or a pharmaceutically acceptable salt thereof, isoniazid or a pharmaceutically acceptable salt thereof, pyrazinamide or a pharmaceutically acceptable salt thereof and ethambutol or a pharmaceutically acceptable salt thereof, wherein rifampin and isoniazid are in separate layers. The invention also provides a pharmaceutical composition prepared therefrom having advantageous stability and bioavailability.

35 Claims, 5 Drawing Sheets

PROCESS FOR PREPARATION OF ANTI-TUBERCULAR COMBINATION AND PHARMACEUTICAL COMPOSITION PREPARED THEREFROM

FIELD OF THE INVENTION

This invention relates to a process for preparing a pharmaceutical composition comprising four antitubercular drugs: rifampin, isoniazid, pyrazinamide and ethambutol hydrochloride, wherein rifampin and isoniazid are in separate layers. The invention also provides a pharmaceutical composition prepared therefrom having advantageous stability and bioavailability.

BACKGROUND OF THE INVENTION

Tuberculosis (TB) is one of the most common infectious diseases known to man. Though effective treatments using four drugs: rifampincin, isoniazid, ethambutol and pyrazinamide are available, the high doses required and the lengthy duration of the treatment has resulted in poor compliance from TB patients. The failure of these anti-tubercular treatments is essentially due to partial compliance or non-compliance with recommended therapy. Moreover, it has been found that partial compliance with recommended therapy results in drug resistance. A patient who receives no therapy at all transmits non-resistant tubercle bacilli to others, whereas a patient who receives partial therapy develops multi-drug resistance and transmits drug-resistant tubercle bacilli. Drug resistance in TB patients predominantly arises as a result of multiple interruptions of treatment. When using single-drug formulations, patients are more prone to interrupt treatment with some drugs and not others, thereby creating a risk of monotherapy and selection of drug-resistant mutations.

To improve patient compliance and control drug resistance, the WHO recommends the use of a fixed-dose combination (FDC). These anti-tuberculosis drugs can be given as single-drug formulations or as fixed-dose combinations in which two or more anti-tuberculosis drugs are present in fixed proportions in the same formulation. In 1999 the WHO recommended a four-drug fixed-dose combination to improve compliance by reducing the number of tablets required to be consumed. Although four-drug FDCs are available, their effectiveness is hampered due to a reduction in the bioavailability of rifampicin in the presence of the other drugs released by the tablets. Various researchers have worked on several aspects of this problem with FDC tablets and several suggestions are recorded in the literature.

WO 02/087547 discloses a wet granulation process for manufacture of tablets containing rifampicin, isoniazid, pyrazinamide and ethambutol HCl by 3-step or 4-step granulation, without use of a surfactant. The 3-step or 4-step granulation shows better dissolution profile of rifampicin than a 2-step granulation process. This might be attributed to the longer disintegration time of the tablets granulated by a 2-step granulation process. Furthermore, the experiment was conducted to study the effect of a surfactant on the composition prepared from the process disclosed in WO 02/087547. The results show that use of a surfactant, such as sodium lauryl sulfate (SLS), affected the in vitro dissolution of rifampicin adversely and the composition without SLS shows better in vitro dissolution of rifampicin.

US 2005/0249804 discloses a composition of rifampicin, isoniazid, pyrazinamide and ethambutol in a stable complex. When the active ingredients are mixed together after treatment, they will not react with each other. The process for preparing said composition needs only wet granulation, drying, mixing and lubricating with surfactant and compression into tablet form. The composition avoids the need for coating the product.

US 2005/0084455 provides a biodegradable inhalable micro-particle composition useful for target-specific drug delivery to manage pulmonary TB. This composition is comprised of two anti-tubercular drugs and a biodegradable polymer in the ratio of 1:2 to 2:1 for drug delivery.

U.S. Pat. No. 7,195,769 discloses an oral pharmaceutical composition comprised of rifampicin and isoniazid, wherein rifampicin is formulated to release in the stomach and isoniazid is formulated for an extended or delayed enteric release so that the release of rifampicin and that of isoniazid take place at separate locations inside the gastrointestinal tract and the bioavailability of rifampicin is enhanced by preventing its degradation caused by the presence of isoniazid.

In view of degradation of rifampicin in an acidic environment, in particular in the presence of isoniazid, the invention of CN 1437946 provides a rifampicin release system wherein rifampicin is released in the intestine while the other drugs, such as isoniazid, pyrazinamide and ethambutol HCl are released in the stomach, or wherein isoniazid is released in the intestine while the other drugs are released in the stomach. CN 1408354 discloses a tablet-in-tablet pharmaceutical composition, wherein the core of the composition comprises rifampicin and the outer layer comprises isoniazid and pyrazinamide to avoid the formation of 3-formyl rifampicin SV isoniazid.

However, there is still a need in develop an anti-tubercular pharmaceutical composition with improved stability and bioavailability.

SUMMARY OF THE INVENTION

The invention provides a process for preparing a film-coated, multi-layered preparation comprising four anti-tubercular drugs: rifampin, isoniazid, pyrazinamide and ethambutol hydrochloride, which comprises the following steps:
(a) individually mixing each of pyrazinamide, isoniazid and ethambutol or each of pharmaceutically acceptable salt thereof with excipients followed by wet granulation of the resulting each mixture with a binder material to obtain granules of said each mixture and thereafter subjecting said granules of each mixture to drying;
(b) mixing rifampin or pharmaceutically acceptable salts thereof with excipients to form a powder;
(c) preparing two to four pharmaceutical layers by mixing granules of isoniazid or a pharmaceutically acceptable salt thereof of step (a) or rifampin or a pharmaceutically acceptable salt thereof of step (b) and 0 to two of granules of pyrazinamide or a pharmaceutical acceptable salt thereof and ethambutol or a pharmaceutically acceptable salt thereof of step a) to form two to four pharmaceutical layers so that rifampin or a pharmaceutically acceptable salt thereof and isoiazid or a pharmaceutically acceptable salt thereof are in different layers,
wherein the two pharmaceutical layers comprise granules of isoniazid or a pharmaceutical acceptable salt thereof in one layer, rifampin or a pharmaceutical acceptable salt thereof in the other layer and granules of pyrazinamide or a pharmaceutically acceptable salt thereof and ethambutol HCl or a pharmaceutically acceptable salt thereof in either layer,
wherein the three pharmaceutical layers comprise granules of isoniazid or a pharmaceutically acceptable salt thereof in one layer, rifampin or a pharmaceutically acceptable salt thereof in another layer and granules of pyrazinamide or a pharmaceutically acceptable salt thereof and ethambutol or a pharmaceutically acceptable salt thereof in any layer to form three pharmaceutical layers, or wherein the four pharmaceutical layers comprise granules of isoniazid or a pharmaceutically acceptable salt thereof, rifampin or a pharmaceutically acceptable salt thereof, granules of pyrazinamide or a pharmaceutically acceptable salt thereof, and granules of ethambutol or a pharmaceutical acceptable salt thereof present in four separate layers; and (d) compressing the pharmaceutical layers of (c) to obtain a multi-layered preparation.

The invention also provides a film-coated, multi-layered pharmaceutical composition comprising anti-tubercular drugs: rifampin, isoniazid, pyrazinamide and ethambutol or pharmaceutically acceptable salts thereof, in which rifampin and isoniazid or pharmaceutically acceptable salts thereof are present in separate layers and the moisture content of the pharmaceutical composition is less than 2.0%.

DETAILED DESCRIPTION OF THE INVENTION

Figure 1:
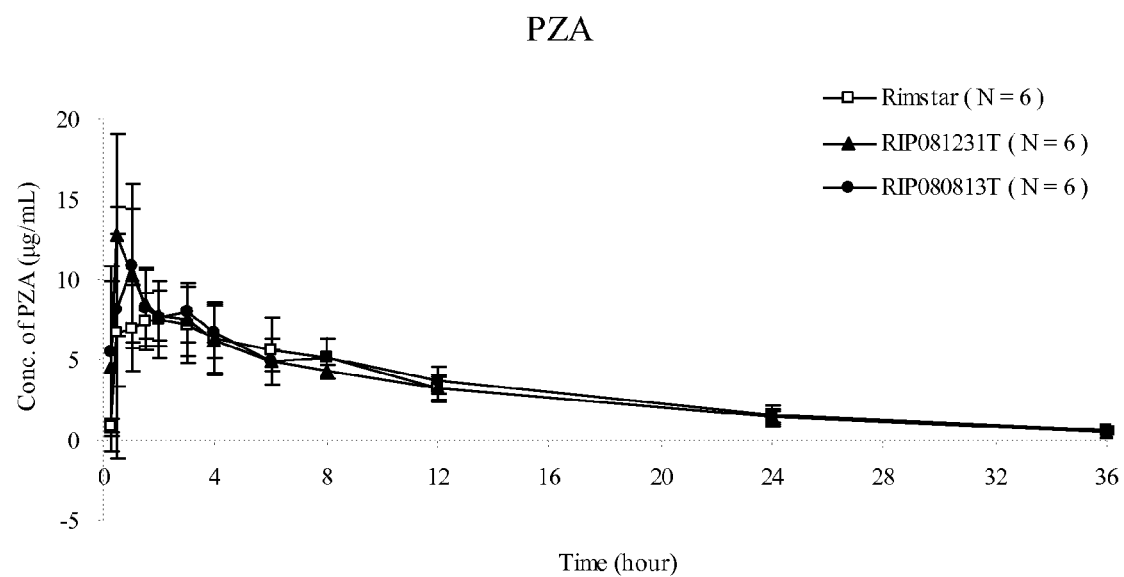
FIG. 1 shows the blood concentration of pyrazinamide of RIP080813T, RIP081231T and RIMSTAR®.

The invention is based on a discovery of an improved process for preparing an anti-tubercular pharmaceutical composition comprising rifampin, isoniazid, pyrazinamide and ethambutol hydrochloride which results in excellent stability and bioavailability of the active ingredients and which is characterized by the presence of rifampin and isoniazid in separate layers to avoid the degradation of rifampin and isoniazid.

In one aspect, the invention provides a process for preparing a film-coated, multi-layered preparation comprising four anti-tubercular drugs: rifampin, isoniazid, pyrazinamide and ethambutol hydrochloride, which comprises the following steps:

(a) individually mixing each of pyrazinamide, isoniazid and ethambutol or each of pharmaceutically acceptable salts thereof with excipients followed by wet granulation of the resulting each mixture with a binder material to obtain granules of said each mixture and thereafter subjecting said granules of each mixture to drying;

(b) mixing rifampin or pharmaceutically acceptable salts thereof with excipients to form a powder;

(c) preparing two to four pharmaceutical layers by mixing granules of isoniazid or a pharmaceutically acceptable salt thereof of step (a) or rifampin or a pharmaceutically acceptable salt thereof of step (b) and 0 to two of granules of pyrazinamide or a pharmaceutical acceptable salt thereof and ethambutol or a pharmaceutically acceptable salt thereof of step a) to form two to four pharmaceutical layers so that rifampin or a pharmaceutically acceptable salt thereof and isoiazid or a pharmaceutically acceptable salt thereof are in different layers, wherein the two pharmaceutical layers comprise granules of isoniazid or a pharmaceutical acceptable salt thereof in one layer, rifampin or a pharmaceutical acceptable salt thereof in the other layer and granules of pyrazinamide or a pharmaceutically acceptable salt thereof and ethambutol HCl or a pharmaceutically acceptable salt thereof in either layer, wherein the three pharmaceutical layers comprise granules of isoniazid or a pharmaceutically acceptable salt thereof in one layer, rifampin or a pharmaceutically acceptable salt thereof in another layer and granules of pyrazinamide or a pharmaceutically acceptable salt thereof and ethambutol or a pharmaceutically acceptable salt thereof in any layer to form three layers, or wherein the four pharmaceutical layers comprise granules of isoniazid or a pharmaceutically acceptable salt thereof, rifampin or a pharmaceutically acceptable salt thereof, granules of pyrazinamide or a pharmaceutically acceptable salt thereof, and granules of ethambutol or a pharmaceutical acceptable salt thereof in four separate layers; and (d) compressing the pharmaceutical layers of (c) to obtain a multi-layered preparation.

According to the invention, rifampin or a pharmaceutically acceptable salt thereof is in powder form.

In one embodiment, the process further comprises the following step:

(e) subcoating the preparation of step (d) with a subcoating solution containing subcoating materials and a solvent that comprises organic solvent and water in a ratio of about 50% to 100%:0% to 50%.

In a further embodiment, in addition to step (e), the process of the invention further comprises the following step:

(f) overcoating the subcoated preparation of step (e) to obtain a film-coated, multi-layered preparation.

Steps (a) and (b) of the Process of the Invention

According to the process of the invention, pyrazinamide, isoniazid and ethambutol or a pharmaceutically acceptable salt thereof are mixed with excipients and then subjected to granulation procedure and drying. Preferably, the drying is performed until the moisture content is less than about 5% to form granules. More preferably, the drying is performed until the moisture content is less than about 3%, about 2%, about 1%, about 0.5% or about 0.2%. However, rifampin or a pharmaceutically acceptable salt thereof is only mixed with excipients to form a powder but not subject to granulation procedure.

According to the invention, the phrase "pharmaceutically acceptable salt(s)", as used herein, means those salts of compounds (i.e., pyrazinamide, isoniazid and ethambutol and rifampin) of the invention that are safe and effective for use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

According to the invention, pyrazinamide, isoniazid and ethambutol and rifampin or a pharmaceutically acceptable salt are commercially available. The suppliers of the above compounds can be found from the website: www.icis.com/Search/default.aspx.

The granules obtained by wet granulation with a binder material are dried at a temperature between about 40 to about 80° C., preferably between about 50 to about 60° C.

According to one embodiment of the present invention, the granulation is dried at about 40 to about 60° C. in a suitable fluid. Preferably, the moisture content of the granules is below about 5%, preferably below about 3%, about 2%, about 1%, about 0.5% or about 0.2% as determined by a moisture balance or equivalent. According to a preferred embodiment of the invention, the granule moisture content measurements are made by the application of infrared (IR) at 70° C.

According to one embodiment of the invention, the process further comprises a step of mixing the granules of step a) with excipients.

The binder material used herein refers to any material that is added to pharmaceutical compositions to help hold such compositions together and release the medicament therefrom. Suitable binder materials which can be used in the process of the present invention include gelatin, starch, povidone, hydroxypropylmethyl cellulose, hydroxypropyl cellulose, pregelatinized starch, sucrose, acacia, alginic acid, sodium alginate and the like. The preferred binder material is povidone.

According to the present invention, the binder material is dissolved in organic solvents including but not limited to high-concentration alcohol. Preferably, the concentration of alcohol is at least about 95%. More preferably, the concentration of alcohol is 99.5%.

In addition to binder materials, the excipients which can be used in the process of the present invention include one or more antioxidants, inert diluents, disintegrants and conventional additives such as lubricating agents, coloring agents or coating materials.

The inert diluents which can be used in the process of the present invention include calcium carbonate, calcium sulfate, dextrates, dibasic calcium phosphate, magnesium carbonate, magnesium oxide, lactose, mannitol, microcrystalline cellulose, starch, polymethacrylates and the like.

The antioxidants which can be used in the process of the present invention include sodium metabisulphite, sodium sulphite, α-tocopherol, ascorbic acid, sodium ascorbate, malic acid, propylgallate and the like.

The lubricating agent as used herein refers to a substance added to the dose to enable the dose, e.g., a tablet, to be released from the mold or die after it has been compressed. Suitable lubricating agents which can be used in the process of the present invention include talc, magnesium sterate, calcium stearate, stearic acid, colloidal silicon dioxide, hydrogenated vegetable oil and the like. The preferred lubricating agent is magnesium stearate.

The disintegrants which can be used in the process of the present invention include crospovidone, sodium starch glycollate, croscarmellose sodium, microcrystalline cellulose and the like.

Step (c) of the Process of the Invention

According to one embodiment of the invention, the process of the invention provides a film-coated, multiple-layered tablet containing rifampin, isoniazid, pyrazinamide and ethambutol or a pharmaceutically acceptable salt thereof prepared by the processes described above wherein rifampin or a pharmaceutically acceptable salt and isoniazid or a pharmaceutically acceptable salt are present in separate layers.

In one preferred embodiment of the invention, the pharmaceutical composition comprising rifampin, isoniazid, ethambutol and pyrazinamide or a pharmaceutically acceptable salts thereof in fixed-dose combination is formulated so that rifampin or a pharmaceutically acceptable salt thereof alone is present in one layer and isoniazid, ethambutol and pyrazinamide or a pharmaceutically acceptable salt thereof are present in another layer.

In another preferred embodiment of the invention, the pharmaceutical composition comprising rifampin, isoniazid, ethambutol and pyrazinamide or pharmaceutically acceptable salts thereof in fixed-dose combination is formulated as two layers so that rifampin or a pharmaceutically acceptable salt thereof and either of ethambutol or a pharmaceutically acceptable salt thereof or pyrazinamide or a pharmaceutically acceptable salt thereof are present in one layer and isoniazid or a pharmaceutically acceptable salt thereof and either of ethambutol or a pharmaceutically acceptable salt thereof (if pyrazinamide or a pharmaceutically acceptable salt thereof is formulated with rifampin or a pharmaceutical acceptable salt thereof) or pyraninamide or a pharmaceutically acceptable salt thereof (if ethambutol or a pharmaceutically acceptable salt thereof is formulate with rifampin or a pharmaceutically acceptable salt thereof) are present in another layer. Preferably, ethambutol is in the form of hydrochloride salt.

In another preferred embodiment of the invention, the pharmaceutical composition comprising rifampin or a pharmaceutically acceptable salt thereof, isoniazid or a pharmaceutically acceptable salt thereof, ethambutol or a pharmaceutically acceptable salt thereof and pyrazinamide or a pharmaceutically acceptable salt thereof in fixed-dose combination is formulated as three layers so that rifampin or a pharmaceutically acceptable salt thereof and either of ethambutol or a pharmaceutically acceptable salt thereof or pyrazinamide or a pharmaceutically acceptable salt thereof are present in one layer; isoniazid or a pharmaceutically acceptable salt thereof is in another layer; and either of ethambutol or a pharmaceutically acceptable salt thereof (if pyrazinamide or a pharmaceutically acceptable salt thereof is formulated with rifampin or a pharmaceutically acceptable salt thereof) or pyraninamide or a pharmaceutically acceptable salt thereof (if ethambutol or a pharmaceutically acceptable salt thereof is formulate with rifampin or a pharmaceutically acceptable salt thereof) alone is present in the third layer.

In another preferred embodiment of the invention, the pharmaceutical composition comprising rifampin or a pharmaceutically acceptable salt thereof, isoniazid or a pharmaceutically acceptable salt thereof, ethambutol or a pharmaceutically acceptable salt thereof and pyrazinamide or a pharmaceutically acceptable salt thereof in fixed-dose combination is formulated as four layers so that rifampin or a pharmaceutically acceptable salt thereof, ethambutol or a pharmaceutically acceptable salt thereof, isoniazid or a pharmaceutically acceptable salt thereof and pyrazinamide or a pharmaceutically acceptable salt thereof are present in separate layers.

According to one embodiment of the invention, the film-coated, multi-layered tablet comprises two pharmaceutical layers in the following combinations:
  (a) rifampin, pyrazinamide granules and ethambutol granules are in one layer and isoniazid granules are in the other layer;
  (b) rifampin and pyrazinamide granules are in one layer and isoniazid granules and ethambutol granules are in the other layer;
  (c) rifampin and ethambutol granules are in one layer and isoniazid granules and pyrazinamide granules are in the other layer; or (d) isoniazid granules, pyrazinamide granules and ethambutol granules are in one layer and rifampin are in the other layer.

According to the invention, rifampin is in powder form. Preferably, ethambutol is in the form of hydrochloride salt.

According to one embodiment of the invention, the film-coated, multi-layered tablet comprises three pharmaceutical layers in the following combinations:
(a) rifampin is in one layer, isoniazid granules are in another layer and pyrazinamide granules and ethambutol granules are in the third layer;
(b) rifampin and pyrazinamide granules are in one layer, isoniazid granules are in another layer and ethambutol granules are in the third layer;
(c) rifampin and ethambutol granules are in one layer, isoniazid granules are in another layer and pyrazinamide granules are in the third layer;
(d) isoniazid granules and pyrazinamide granules are in one layer, rifampin is in another layer and ethambutol granules are in the third layer; or
(e) isoniazid granules and ethambutol granules are in one layer, rifampin is in another layer and pyrazinamide granules are in the third layer.

According to the invention, rifampin is in powder form. Preferably, ethambutol is in the form of hydrochloride salt.

According to one embodiment of the invention, the film-coated, multi-layered tablet comprises four pharmaceutical layers, wherein rifampin, pyrazinamide granules, isoniazid granules and ethambutol granules are in separate four layers.

Step (d) of the Process of the Invention

According to the invention, the pharmaceutical layers of step (c) are compressed into a preparation, wherein the compression is conducted by any methods known in the art. Persons skilled in the art can proceed with the compressing step though any standard methods or techniques well known to those skilled in the art.

According to one embodiment of the invention, rifampin, isoniazid, pyrazinamide and ethambutol hydrochloride in a tablet prepared by the process are in FDC.

Preferably, the amounts of rifampin, ethambutol HCl, isoniazid and pyrazinamide of the FDC pharmaceutical preparations of the invention are 150 mg, 275 mg, 75 mg and 400 mg, respectively, in one preparation. More preferably, the amounts of rifampin, ethambutol HCl, isoniazid and pyrazinamide of the FDC pharmaceutical preparations of the invention are 75 mg, 137.5 mg, 37.5 mg and 200 mg, respectively, in one tablet.

Steps (e) and (f) of the Process of the Invention

According to the present invention, the process of the present invention can further comprise a step of subcoating. After the subcoating, an overcoating step can be further included. The coating materials which can be used in the process of the present invention include hydroxypropyl methylcellulose (HPMC), polyvinyl alcohol, ethyl cellulose, methacrylic acid copolymers, cellulose acetate phthalate, cetyl alcohol, shellac, microcrystalline wax, Opadry AMB and the like. For subcoating, the preferred coating material is HPMC; for overcoating, the preferred coating material is Opadry AMB.

According to the present invention, the subcoating material is dissolved in a solvent which is comprised of organic solvent and water in a ratio of about 50%-100%:about 0%-50%. Preferably, the ratio is about 60%-100%:about 0%-40%, about 70%-100%:about 0% to 30%, about 80%-100%:0%-20%, about 90%-100%:about 0% to 10%, about 95%-100%: about 0% to 5%. Suitable organic solvent includes but not limited to ethanol, acetone and dichloromethane. The preferred organic solvent is 95% ethanol. The overcoating material is dissolved in water.

In another aspect, the present invention provides a film-coated, multi-layered pharmaceutical composition comprising anti-tubercular drugs: rifampin, isoniazid, pyrazinamide and ethambutol hydrochloride, in which rifampin and isoniazid are present in separate layers and the moisture content of the pharmaceutical composition is less than 2.0%. Preferably, the moisture content of the pharmaceutical composition ranges from 0.05% to 2%; more preferably, the moisture content ranges from 0.05% to 1.5%, 0.05% to 1%, 0.1% to 2%, 0.1% to 1.5% or 0.1% to 1%. Preferably, the moisture content ranges from 0.1% to 1%.

According to one embodiment of the invention, the moisture content of the pharmaceutical composition is less than 1.0% as determined by a moisture balance or equivalent.

According to one embodiment of the invention, the pharmaceutical composition further comprises excipients selected from one or more of antioxidant, inert diluents, disintegrants and lubricating agents as mentioned above.

According to one embodiment of the invention, the pharmaceutical composition is a two-layered preparation in the following combinations:
(a) rifampin, pyrazinamide granules and ethambutoll granules are in one layer and isoniazid granules are in the other layer;
(b) rifampin and pyrazinamide granules are in one layer and isoniazid granules and ethambutol granules are in the other layer;
(c) rifampin and ethambutol granules are in one layer and isoniazid granules and pyrazinamide granules are in the other layer; or
(d) isoniazid granules, pyrazinamide granules and ethambutol granules are in one layer and rifampin are in the other layer.

According to the invention, rifampin is in powder form. Preferably, ethambutol is in the form of hydrochloride salt.

According to one embodiment of the invention, the pharmaceutical composition is a three-layered preparation in the following combinations:
(a) rifampin is in one layer, isoniazid granule are in another layer and pyrazinamide granules and ethambutol granules are in the third layer;
(b) rifampin and pyrazinamide granules are in one layer, isoniazid granules are in another layer and ethambutol granules are in the third layer;
(c) rifampin and ethambutol granules are in one layer, isoniazid granules are in another layer and pyrazinamide granules are in the third layer;
(d) isoniazid granules and pyrazinamide granules are in one layer, rifampin is in another layer and ethambutol granules are in the third layer; or
(e) isoniazid granules and ethambutol granules are in one layer, rifampin is in another layer and pyrazinamide granules are in the third layer.

According to the invention, rifampin is in powder form. Preferably, ethambutol is in the form of hydrochloride salt.

According to one embodiment of the invention, the pharmaceutical composition is a four-layered preparation, wherein rifampim, pyrazinamide granules, isoniazid granules and ethambutol granules are in separate four layers. Preferably, ethambutol is in the form of hydrochloride salt.

According to one embodiment of the present invention, the pharmaceutical composition is a fixed-dose combination in which the amounts of rifampin, ethambutol, isoniazid and pyrazinamide are 150 mg, 275 mg, 75 mg and 400 mg, respectively. More preferably, the amounts of rifampin, ethambutol, isoniazid and pyrazinamide are 75 mg, 137.5 mg, 37.5 mg and 200 mg, respectively. Preferably, ethambutol is in the form of hydrochloride salt.

More preferably, the pharmaceutical composition of the present invention is prepared from the methods of the invention. More preferably, the pharmaceutical composition of the present invention is prepared from the methods of the invention.

The preparations prepared according to the process of the invention have advantageous stability of rifampin and isoniazid. In addition to the stability, the preparations have superior bioavailability.

EXAMPLE

In the examples, "RIP080831T" and "RIP08123T" are used to illustrate the pharmaceutical compositions and process of the invention. RIP080831T comprise 75 mg of rifampin, 37.5 mg of isoniazid, 200 mg of pyrazinamide and 137.5 mg of ethambutol hydrochloride. RIP08123T comprises 150 mg of rifampin, 75 mg of isoniazid, 400 mg of pyrazinamide and 275 mg of ethambutol hydrochloride. RIMSTAR® is a commercial product which also comprises 150 mg of rifampin, 75 mg of isoniazid, 400 mg of pyrazinamide and 275 mg of ethambutol hydrochloride and is used as comparative example.

Example 1

Process for Preparation of Two-Layered Four-Drug FDC Compositions

The drugs rifampin, isoniazid, pyrazinamide and ethambutol HCl were available to persons skilled in the art. For example, rifampin, isoniazid, pyrazinamide and ethambutol HCl are available from BTX Global Pharmaceuticals, Inc. (New Jersey, US), F. Hoffmann-La Roche Ltd, (New Jersey, US); Pharmchem Co., (New Delhi, India) and CBC (America) Corp, (New York, US), respectively. The ingredients and specific amounts thereof are listed in below tables.

TABLE 1

Formulation of RIP081231T

| Item | Ingredient | % w/w |
|---|---|---|
| Layer-I | | |
| 1 | Rifampin | 14.02% |
| 2 | Magnesium hydroxide | 0.93% |
| 3 | Magnesium sterate | 0.93% |
| 4 | Granules-placebo | 7.95% |
| subtotal | | 23.83% |
| Layer-II | | |
| 5 | polyethylene glycol | 0.94% |
| 6 | Granules-ISN, EBT | 75.23% |
| Subtotal | | 76.17% |
| Total | | 100.00% |
| Granules-placebo | | |
| 7 | Sodium starch glycolate | 4.68% |
| 8 | Polyvinylpyrrolidone | 1.40% |
| 9 | Croscamellose sodium | 1.87% |
| subtotal | | 7.95% |

TABLE 1-continued

Formulation of RIP081231T

| Item | Ingredient | % w/w |
|---|---|---|
| Granules-ISN, EBT | | |
| 11 | Isoniazid | 7.01% |
| 12 | Pyrazinamide | 37.38% |
| 13 | Ethambutol HCl | 25.70% |
| 15 | Polyvinylpyrrolidone | 2.34% |
| 16 | Croscamellose sodium | 2.80% |
| subtotal | | 75.23% |

TABLE 2

Formulation of RIP080813T

| Item | Ingredient | % w/w |
|---|---|---|
| Layer-I | | |
| 1 | Rifampin | 12.50% |
| 2 | Magnesium hydroxide | 1.17% |
| 3 | poloxamer | 1.08% |
| 4 | Magnesium sterate | 0.75% |
| 5 | Granules-Pyz | 44.50% |
| subtotal | | 60.00% |
| Layer-II | | |
| 6 | polyethylene glycol | 2.73% |
| 7 | Iron Oxide Red | 0.26% |
| 8 | Iron Oxide Yellow | 0.01% |
| 9 | Granules-ISN, EBT | 37.00% |
| Subtotal | | 40.00% |
| Total | | 100.00% |
| Granules-Pyz | | |
| 10 | Pyrazinamide | 33.33% |
| 11 | sodium starch glycolate | 3.50% |
| 12 | Polyvinylpyrrolidone | 1.50% |
| 13 | Croscamellose sodium | 6.17% |
| Subtotal | | 44.50% |
| Granules-ISN, EBT | | |
| 14 | Isoniazid | 6.25% |
| 15 | Ethambutol HCl | 22.92% |
| 16 | sodium starch glycolate | 2.50% |
| 17 | Polyvinylpyrrolidone | 1.17% |
| 18 | Croscamellose sodium | 4.17% |
| Subtotal | | 37.00% |

The process for preparation of the two-layered four-drug FDC compositions of the invention is described below.

Granulation of Pyrazinamide

1. Dissolve polyvinylpyrrolidone in 99.5% alcohol with a constant stir.
2. Slightly mix pyrazinamide, sodium starch glycolate and Croscamellose Sodium and sieve them by 40 mesh.
3. Granulate the blend from step 2 with the dispersion from step 1 in a super mixer.
4. Dry the wet granulation at about 50° C. in a suitable fluid bed processor for about 120 minutes so that the moisture content of the granule-Pyz is less than 5.0% as determined by a moisture balance or equivalent.

Granulation of Isoniazid and Ethambutol HCl
1. Dissolve polyvinylpyrrolidone in 99.5% alcohol with a constant stir.
2. Slightly mix Isoniazid, Ethambutol HCl, sodium starch glycolate and Croscamellose Sodium and sieve them by 40 mesh.
3. Granulate the blend from step 6 with the dispersion from step 5 in a super mixture at a rate of 2/10 sec.
4. Dry the wet granulation at about 50° C. in a suitable fluid bed processor for about 120 minutes so that the moisture content of the granule-ISN, EBT is less than 5.0% as determined by a moisture balance or equivalent.

Preparation of Layer 1
1. Mix rifampin, magnesium hydroxide, poloxamer, magnesium sterate and pyrazinamide granules as layer 1.

Preparation of Layer 2
1. Mix poloxamer, Iron Oxide Red, Iron Oxide Yellow and granule-ISN, EBT as layer 2.

Subcoating
1. Dissolve coating materials in solvent comprised of organic solvent and water in a ratio of about 95%-100%:about 0% to 5% and disperse colorant in an organic solvent by homogenizer, wherein the organic solvent is alcohol. Mix coating solution and colorant solution and keep stirring.

Overcoating:
1. Dissolve coating materials in a solvent.
2. Disperse the coating solution by stirring overnight.
3. Screen the solution with 100 mesh before starting the coating process.

Example 2

Stability Test of the Composition of the Invention

Stability test was conducted by using RIP080813T tablets prepared in Example 1 under the conditions described in the guidelines of International Conference on Harmonisation. The conditions of the long-term test were 25° C. and 60% RH. The conditions of the accelerated test were 40° C. and 75% RH. The results are shown in Table 1 below.

TABLE 1

| | Conditions of Accelerated Test | | | |
|---|---|---|---|---|
| Period | Rifampin | Isoniazid | Pyrazinamide | Ethambutol HCL |
| Initial (0 month) | 101.2 | 99.81 | 99.56 | 97.50 |
| 3 months 40° C., RH: 75% | 99.29 | 100.83 | 100.70 | 97.85 |
| 3 months 25° C., RH: 60% | 100.08 | 97.98 | 98.71 | 98.50 |
| 6 months 40° C., RH: 75% | 102.36 | 99.05 | 99.49 | 98.21 |
| 6 months 25° C., RH: 60% | 101.21 | 98.27 | 99.25 | 98.53 |

As shown in the table, the FDC composition of the present invention exhibits excellent stability.

Example 3

In Vivo Pharmacokinetic Studies on Humans

A clinical trial was conducted. The subjects were divided into three groups for testing of RIP080813T, RIP081231T (the compositions of the invention in Example 1) and Rismstar® respectively.

Before dosing, 10 ml of blood was collected from each subject as a blank. In the trial, the subjects were given two tablets of RIP080813T, one tablet RIP081231T and one tablet of RIMSTAR® at different times and 10 ml of blood was collected from each subject. Pharmacokinetic parameters (Cmax and AUC) for rifampin, isoniazid, pyrazinamide and ethambutol HCl were calculated from blood concentrations obtained at various time intervals (i.e., at 0.25, 0.5, 1, 1.5, 2, 3, 4, 6, 8, 12, 24 and 36 hour) after dosing.

The results shown in Table 3 below demonstrate that RIP080813T and RIP081231T of the present invention provides equivalent or higher Cmax and AUC of isoniazid, rifampun and ethambutol as compared to RIMSTAR®.

TABLE 2

Pharmacokinetic parameters of rifampin, isoniazid, pyrazinamide and ethambutol HCl of RIP080813T and RIP081231T of the present invention and RIMSTAR ®

| Ingredient | Drug | Tmax (hr) | Cmax (μg/mL) | AUC 0-∞ (hr * μg/mL) |
|---|---|---|---|---|
| PZA | RIMSTAR ® | 1.58 ± 0.97 | 10.85 ± 5.46 | 112.57 ± 27.24 |
| | RIP080813T | 0.83 ± 0.26 | 12.37 ± 5.09 | 123.24 ± 29.61 |
| | RIP081231T | 0.71 ± 0.46* | 14.98 ± 4.44 | 112.14 ± 22.61 |
| INH | RIMSTAR ® | 1.25 ± 0.69 | 0.59 ± 0.56 | 1.16 ± 0.63 |
| | RIP080813T | 0.58 ± 0.34* | 0.82 ± 0.44 | 1.37 ± 0.58 |
| | RIP081231T | 0.54 ± 0.25* | 1.11 ± 0.51 | 1.50 ± 0.68 |
| EMB | RIMSTAR ® | 3.17 ± 1.17 | 0.61 ± 0.18 | 4.00 ± 1.23 |
| | RIP080813T | 2.17 ± 0.68 | 0.86 ± 0.31 | 4.97 ± 2.21 |
| | RIP081231T | 2.00 ± 0.84 | 0.81 ± 0.27 | 4.69 ± 1.90 |
| RMP | RIMSTAR ® | 2.92 ± 1.02 | 1.75 ± 0.41 | 8.75 ± 2.05 |
| | RIP080813T | 1.75 ± 0.69* | 2.58 ± 1.04 | 9.83 ± 1.87 |
| | RIP081231T | 1.25 ± 0.42** | 1.83 ± 0.90 | 6.80 ± 2.17 |

Figure 2:
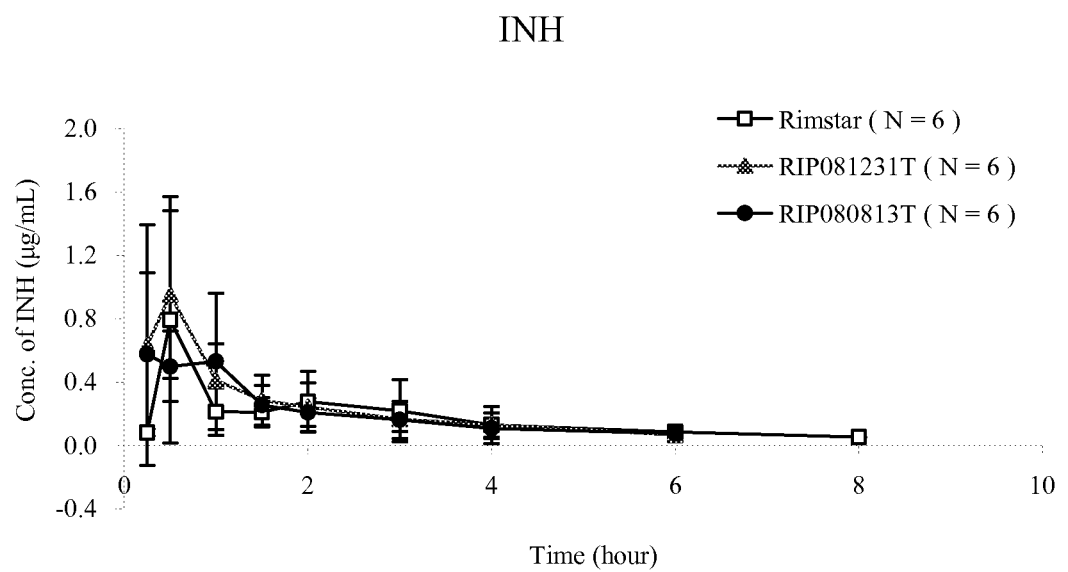
FIG. 2 shows the blood concentration of isoniazid of RIP080813T, RIP081231T and RIMSTAR®.
Figure 3:
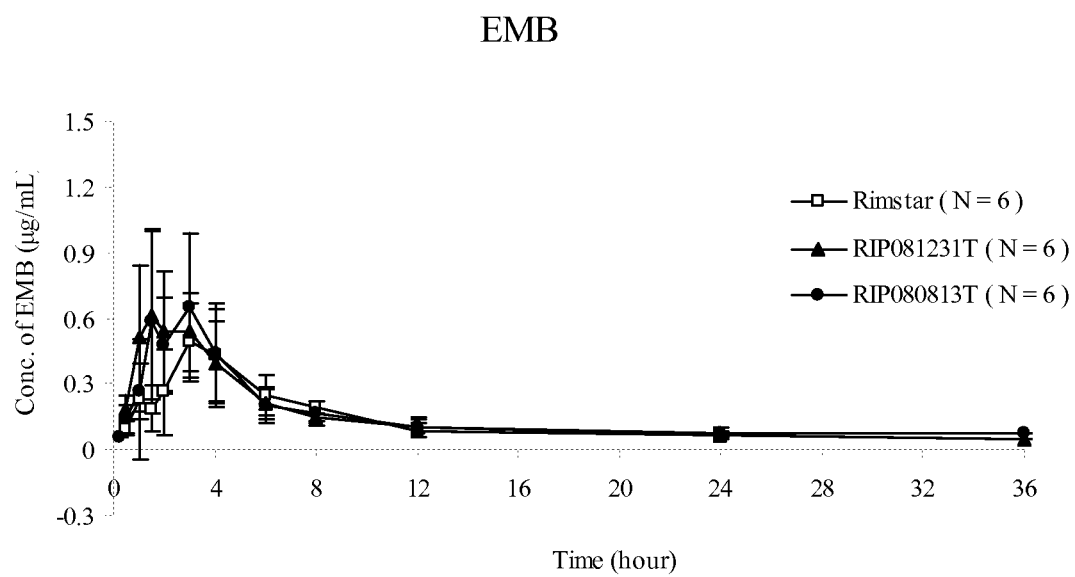
FIG. 3 shows the blood concentration of ethambutol of RIP080813T, RIP081231T and RIMSTAR®.
Figure 4:
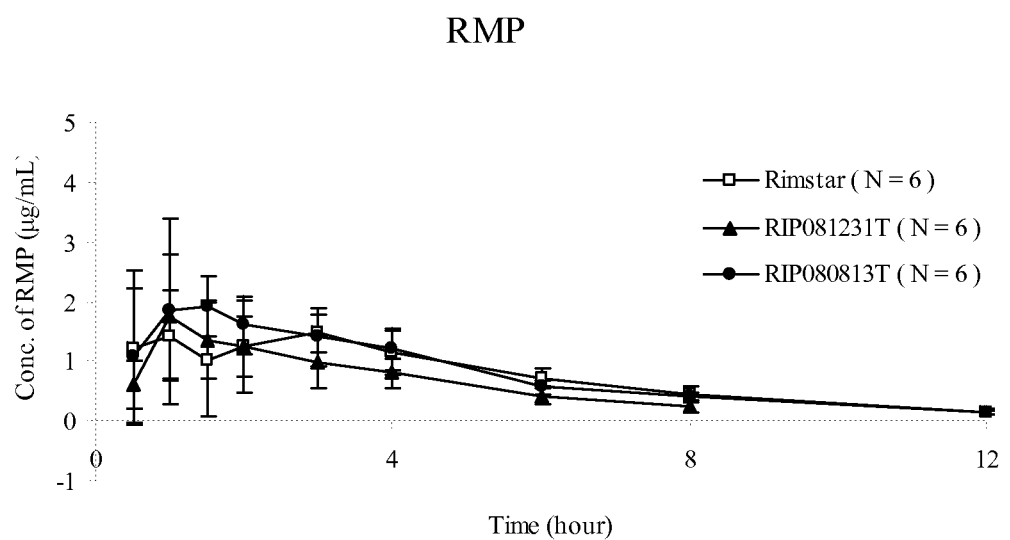
FIG. 4 shows the blood concentration of rifampicin of RIP080813T, RIP081231T and RIMSTAR®.

AUC means area under the time-concentration curve.
Cmax means maximum drug concentration.
Tmax means the time after administration of a drug when the maximum plasma concentration is reached.
PZA: pyrazinamide;
INH: isoniazid;
EMB: ethambutol hydrochloride;
RMP: rifampin
Comparison was made using One-Way ANOVA
*$p < 0.05$,
**$p < 0.01$,
*** $p < 0.001$ FIGS. 1 to 4 show the concentrations of pyrazinamide, isoniazid, ethambutol and rifamoicin in blood of the subjects taking RIP080813T, RIP08123T and RIMSTAR®. FIG. 1 shows that the Cmax of pyrazinamide of RIP080813T is 14% higher than that of RIMSTAR®, while the Cmax of pyrazinamide of RIP08123T is 38% higher than that of RIMSTAR®. The AUC and elimination half life of RIP080813T, RIP08123T are similar to those of RIMSTAR®. FIG. 2 shows that the Cmax of isoniazid of RIP080813T and RIP08123T is slight higher than that of RIMSTAR®. The AUC of RIP080813T, RIP08123T are similar to that of RIMSTAR®. FIG. 3 shows that the highest Cmax of ethambutol for RIP080813T and RIP08123T is about 40% higher than that of RIMSTAR®. The AUC of ethambutol of RIP080813T is 24% larger than that of RIMSTAR®, while the ethambutol of RIP08123T is 17% higher than that of RIMSTAR®. FIG. 4 shows that the Cmax of rifampicin of RIP080813T and RIP08123T is slightly higher than that of RIMSTAR®. The AUC of RIP08123T is similar to that of RIMSTAR®.

Example 4

Dissolution Test

Figure 5:
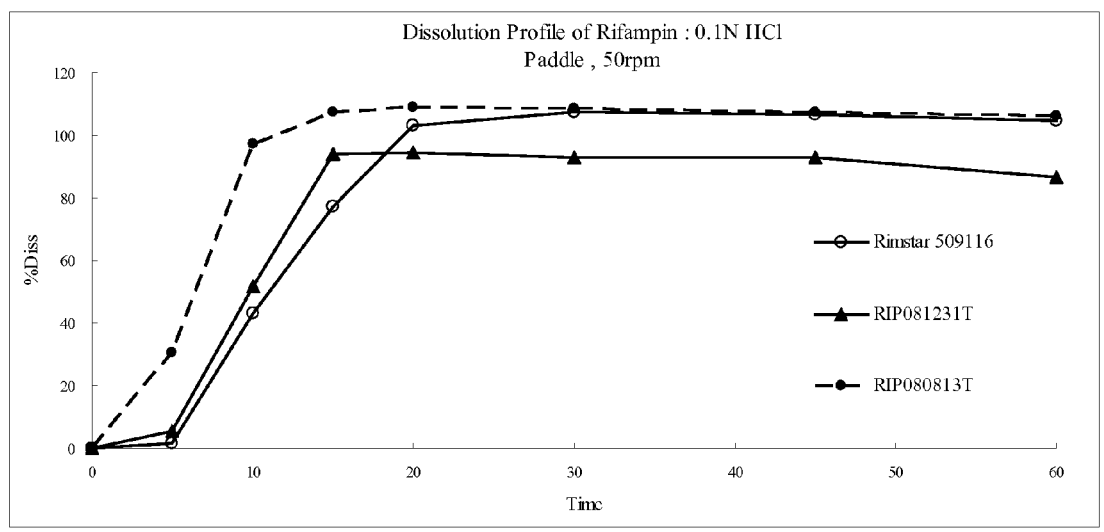
FIG. 5 shows dissolution data of the composition of the invention and RIMSTAR®.

A comparative test for dissolution of RIP080813T and RIP081231T of the present invention and RIMSTAR® was conducted. Hydrochloric acid (0.1 N, pH 1.2) was used as the dissolution media. The temperature of the dissolution medium was maintained at 37° C.±0.5° C., and the agitation speed of the paddle was 50 rpm. The tablets of the above-mentioned drugs were dissolved in the dissolution media under the above-mentioned conditions. The amount of dissolved Rifampin was measured at the wavelength of maximum absorbance at about 475 nm. The results are shown in FIG. 5. Apparently, the RIP080813T and RIP081231T of the present invention have superior dissolution than RIMSTAR®.

What is claimed is:

1. A process for preparing a film-coated, multi-layered preparation comprising four anti-tubercular drugs: rifampin, isoniazid, pyrazinamide and ethambutol hydrochloride, which comprises the following steps:
   (a) individually mixing each of pyrazinamide, isoniazid and ethambutol or each of pharmaceutically acceptable salts thereof with excipients followed by wet granulation of the resulting each mixture with a binder material to obtain granules of said each mixture and thereafter subjecting said granules of each mixture to drying;
   (b) mixing rifampin or pharmaceutically acceptable salts thereof with excipients to form a powder;
   (c) preparing two to four pharmaceutical layers by mixing granules of isoniazid or a pharmaceutically acceptable salt thereof of step (a) or rifampin or a pharmaceutically acceptable salt thereof of step (b) and 0 to two pharmaceutical layers comprised of granules of
      pyrazinamide or a pharmaceutical acceptable salt thereof and ethambutol or a pharmaceutically acceptable salt thereof of step (a) to form two to four pharmaceutical layers so that rifampin or a pharmaceutically acceptable salt thereof and isoniazid or a pharmaceutically acceptable salt thereof are in different layers,
      wherein the two pharmaceutical layers comprise granules of isoniazid or a pharmaceutical acceptable salt thereof in one layer, rifampin or a pharmaceutical acceptable salt thereof in the other layer and granules of pyrazinamide or a pharmaceutically acceptable salt thereof and ethambutol HCl or a pharmaceutically acceptable salt thereof in either layer,
      wherein the three pharmaceutical layers comprise granules of isoniazid or a pharmaceutically acceptable salt thereof in one layer, rifampin or a pharmaceutically acceptable salt thereof in another layer and granules of pyrazinamide or a pharmaceutically acceptable salt thereof and ethambutol or a pharmaceutically acceptable salt thereof in any layer to form three layers, or
      wherein the four pharmaceutical layers comprise granules of isoniazid or a pharmaceutically acceptable salt thereof, rifampin or a pharmaceutically acceptable salt thereof, granules of pyrazinamide or a pharmaceutically acceptable salt thereof, and granules of ethambutol or a pharmaceutical acceptable salt thereof in four separate layers; and
   (d) compressing the pharmaceutical layers of (c) to obtain a multi-layered preparation, wherein the moisture content of the preparation is less than 1.5%.

2. The process of claim 1 further comprising step (e) subcoating the preparation of step (d) with a subcoating solution containing subcoating materials and a solvent that comprises organic solvent and water in a ratio of about 50%-100% : about 50% to 0%.

3. The process of claim 2, wherein the solvent comprises organic solvent and water in a ratio of about 60%-100% : about 0%-40%, about 70%-100% :
   about 0% to 30%, about 80%-100% : 0%-20%, about 90%-100% : about 0% to 10%, or about 95%-100% : about 0% to 5%.

4. The process of claim 2 further comprising step (f) overcoating the subcoated preparation of step (e) to obtain a film-coated, multi-layered preparation.

5. The process of claim 1, wherein the granules are dried in an oven at a temperature between 40 to 80° C.

6. The process of claim 1, wherein the granules are dried in an oven at a temperature between 50 to 60° C.

7. The process of claim 1, wherein the moisture content of the granules is below about 5%.

8. The process of claim 1, wherein the moisture content of the granules is below about 3%, about 2%, about 1%, about 0.5% or about 0.2%.

9. The process of claim 1 wherein the binder material is dissolved in high-concentration alcohol, preferably 95% ethanol.

10. The process of claim 1, wherein the organic solvent for dissolving subcoating material is high-concentration ethanol, preferably 95% ethanol.

11. The process of claim 1, wherein the excipients are antioxidants, inert diluents, disintegrants or lubricating agents.

12. The process of claim 1, wherein the film-coated, multi-layered preparation comprises two pharmaceutical layers comprising rifampin or a pharmaceutically acceptable salt thereof, the granules of pyrazinamide or a pharmaceutically acceptable salt thereof and the granules of ethambutol or a pharmaceutically acceptable salt thereof in one layer and the granules of isoniazid or a pharmaceutically acceptable salt thereof in the other layer.

13. The process of claim 1, wherein the film-coated, multi-layered preparation comprises two pharmaceutical layers comprising rifampin or a pharmaceutically acceptable salt thereof and the granules of pyrazinamide or a pharmaceutically acceptable salt thereof in one layer and the granules of isoniazid or a pharmaceutically acceptable salt thereof and the granules of ethambutol or a pharmaceutically acceptable salt thereof in the other layer.

14. The process of claim 1, wherein the film-coated, multi-layered preparation comprises two pharmaceutical layers comprising rifampin or a pharmaceutically acceptable salt thereof and the granules of ethambutol or a pharmaceutically acceptable salt thereof in one layer and the granules of isoniazid or a pharmaceutically acceptable salt thereof and granules of pyrazinamide or a pharmaceutically acceptable salt thereof in the other layer.

15. The process of claim 1, wherein the film-coated, multi-layered preparation comprises two pharmaceutical layers comprising the granules of isoniazid or a pharmaceutically acceptable salt thereof, the granules of pyrazinamide or a pharmaceutically acceptable salt thereof and the granules of ethambutol HCl or a pharmaceutically acceptable salt thereof in one layer and rifampin or a pharmaceutically acceptable salt thereof in the other layer.

16. The process of claim 1, wherein the film-coated, multi-layered preparation comprises three pharmaceutical layers comprising rifampin or a pharmaceutically acceptable salt thereof in one layer, the granules of isoniazid or a pharmaceutically acceptable salt thereof in another layer, and the granules of pyrazinamide or a pharmaceutically acceptable salt thereof and the granules of ethambutol or a pharmaceutically acceptable salt thereof in the third layer.

17. The process of claim 1, wherein the film-coated, multi-layered preparation comprises three pharmaceutical layers comprising rifampin or a pharmaceutically acceptable salt thereof and the granules of pyrazinamide or a pharmaceutically acceptable salt thereof in one layer, the granules of isoniazid or a pharmaceutically acceptable salt thereof in another layer, and the granules of ethambutol or a pharmaceutically acceptable salt thereof in the third layer.

18. The process of claim 1, wherein the film-coated, multi-layered preparation comprises three pharmaceutical layers comprising rifampin or a pharmaceutically acceptable salt thereof and the granules of ethambutol or a pharmaceutically acceptable salt thereof in one layer, the granules of isoniazid or a pharmaceutically acceptable salt thereof in another layer, and the granules of pyrazinamide or a pharmaceutically acceptable salt thereof in the third layer.

19. The process of claim 1, wherein the film-coated, multi-layered preparation comprises three pharmaceutical layers comprising the granules of isoniazid or a pharmaceutically acceptable salt thereof and the granules of pyrazinamide or a pharmaceutically acceptable salt thereof in one layer, rifampin or a pharmaceutically acceptable salt thereof in another layer, and the granules of ethambutol or a pharmaceutically acceptable salt thereof in the third layer.

20. The process of claim 1, wherein the film-coated, multi-layered preparation comprises three pharmaceutical layers comprising the granules of isoniazid or a pharmaceutically acceptable salt thereof and the granules of ethambutol or a pharmaceutically acceptable salt thereof in one layer, rifampin or a pharmaceutically acceptable salt thereof in a powder form in another layer, and the granules of pyrazinamide or a pharmaceutically acceptable salt thereof in the third layer.

21. The process of claim 1, wherein the film-coated, multi-layered preparation comprises four pharmaceutical layers comprising rifampin or a pharmaceutically acceptable salt thereof, the granules of pyrazinamide or a pharmaceutically acceptable salt thereof, the granules of isoniazid or a pharmaceutically acceptable salt thereof and the granules of ethambutol or a pharmaceutically acceptable salt thereof in four separate layers.

22. A film-coated, multi-layered pharmaceutical composition comprising anti-tubercular drugs: rifampin or a pharmaceutically acceptable salt thereof, isoniazid or a pharmaceutically acceptable salt thereof, pyrazinamide or a pharmaceutically acceptable salt thereof and ethambutol or a pharmaceutically acceptable salt thereof, in which rifampin or a pharmaceutically acceptable salt thereof is in powder form, and isoniazid or a pharmaceutically acceptable salt thereof, pyrazinamide or a pharmaceutically acceptable salt thereof and ethambutol or a pharmaceutically acceptable salt thereof are in granule form; rifampin or a pharmaceutically acceptable salt thereof and isoniazid or a pharmaceutically acceptable salt thereof are present in separate layers; and the moisture content of the pharmaceutical composition is less than 1.5%.

23. The pharmaceutical composition of claim 22, wherein the moisture content ranges from 0.05% to less than 1.5%.

24. The pharmaceutical composition of claim 22, wherein the moisture content ranges from 0.1% to 1.0%.

25. The pharmaceutical composition of claim 22, which is three-layered.

26. The pharmaceutical composition of claim 25, which is in the following combinations:
(a) rifampin is in one layer, isoniazid granules are in another layer and pyrazinamide granules and ethambutol granules are in the third layer;
(b) rifampin and pyrazinamide granules are in one layer, isoniazid granules are in another layer and ethambutol granules are in the third layer;
(c) rifampin and ethambutol granules are in one layer, isoniazid granules are in another layer and pyrazinamide granules are in the third layer;
(d) isoniazid granules and pyrazinamide granules are in one layer, rifampin is in another layer and ethambutol granules are in the third layer; or
(e) isoniazid granules and ethambutol granules are in one layer, rifampin is in another layer and pyrazinamide granules are in the third layer.

27. The pharmaceutical composition of claim 26, wherein ethambutol is in the form of hydrochloride.

28. The pharmaceutical composition of claim 22, which is four-layered and wherein rifampin, pyrazinamide granules, isoniazid granules and ethambutol granules are in separate four layers.

29. The pharmaceutical composition of claim 22, which is a fixed-dose combination and in which the amounts of rifampin, ethambutol, isoniazid and pyrazinamide are 150 mg, 275 mg, 75 mg and 400 mg, respectively.

30. The pharmaceutical composition of claim 22, which is fixed-dose combination and in which the amounts of rifampin, ethambutol, isoniazid and pyrazinamide are 75 mg, 137.5 mg, 37.5 mg and 200 mg, respectively.

31. The pharmaceutical composition of claim 22, which is two-layered.

32. The pharmaceutical composition of claim 30, which is in the following combinations:
(a) rifampin, pyrazinamide granules and ethambutol granules are in one layer and isoniazid granules are in the other layer;
(b) rifampin and pyrazinamide granules are in one layer and isoniazid granules and ethambutol granules are in the other layer;
(c) rifampin and ethambutol granules are in one layer and isoniazid granules and pyrazinamide granules are in the other layer; or
(d) isoniazid granules, pyrazinamide granules and ethambutol HCl granules are in one layer and rifampin is in the other layer.

33. The pharmaceutical composition of claim 32, wherein ethambutol is in the form of hydrochloride.

34. The pharmaceutical composition of claim 22, which is prepared by the process of claim 1.

35. The pharmaceutical composition of claim 22, wherein the moisture content of the pharmaceutical composition is less than 1.0%.

* * * * *